(12) United States Patent
Alber et al.

(10) Patent No.: US 10,585,081 B2
(45) Date of Patent: Mar. 10, 2020

(54) MEASURING DEVICE

(71) Applicant: Endress+Hauser Conducta GmbH+Co. KG, Gerlingen (DE)

(72) Inventors: Thomas Alber, Stuttgart (DE); Joachim Albert, Leonberg (DE); Ralf Steuerwald, Eberdingen (DE); Michael Hanko, Dresden (DE); Angela Eubisch, Nossen (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 556 days.

(21) Appl. No.: 15/287,138

(22) Filed: Oct. 6, 2016

(65) Prior Publication Data
US 2017/0102370 A1 Apr. 13, 2017

(30) Foreign Application Priority Data

Oct. 9, 2015 (DE) .......................... 10 2015 117 242
Dec. 9, 2015 (DE) .......................... 10 2015 121 460
Sep. 20, 2016 (DE) .......................... 10 2016 117 733

(51) Int. Cl.
*G01N 33/18* (2006.01)
*G01N 21/76* (2006.01)
(Continued)

(52) U.S. Cl.
CPC ............. *G01N 33/18* (2013.01); *G01N 21/76* (2013.01); *G01N 21/78* (2013.01); *G01N 27/27* (2013.01); *G01N 2201/129* (2013.01)

(58) Field of Classification Search
CPC ........ G01N 33/18; G01N 21/76; G01N 21/78; G01N 27/27; G01N 2201/129
See application file for complete search history.

(56) References Cited

U.S. PATENT DOCUMENTS

| 5,459,677 A | 10/1995 | Kowalski et al. |
| 6,281,499 B1 | 8/2001 | Kobayashi et al. |
| 2011/0306856 A1* | 12/2011 | Rule .................... A61B 5/1427 600/310 |

FOREIGN PATENT DOCUMENTS

| AT | 513559 A1 | 5/2014 |
| CN | 1148172 A | 4/1997 |

(Continued)

OTHER PUBLICATIONS

Search Report for German Patent Application No. 10 2015 117 242.9, German Patent Office, dated Aug. 9, 2016, 7 pp.
(Continued)

*Primary Examiner* — Samuel P Siefke
(74) *Attorney, Agent, or Firm* — Christopher R. Powers; PatServe (57) ABSTRACT

A measuring apparatus for determining at least one measurand of a measuring medium includes a first measuring device including a first measuring sensor structured to contact the measuring medium and configured to detect measured values of the at least one measurand, the first measuring device embodied to determine a first measured value that is dependent on the at least one measurand of the measuring medium, a sampling device structured to remove a sample from the measuring medium, a second measuring device including a second measuring sensor and embodied to determine a second measured value that is dependent on the least one measurand of the sample, and an electronic control apparatus configured to receive and process the first and second measured value and to perform a verification, calibration and/or adjustment of the first measuring device using the second measured value.

19 Claims, 2 Drawing Sheets

(51) Int. Cl.
   *G01N 21/78*   (2006.01)
   *G01N 27/27*   (2006.01)

(56) References Cited

FOREIGN PATENT DOCUMENTS

| | | |
|---|---|---|
| CN | 102313572 A | 1/2012 |
| CN | 102445476 A | 5/2012 |
| CN | 103033500 A | 4/2013 |
| CN | 103403526 A | 11/2013 |
| DE | 1022822 B | 1/1958 |
| DE | 3926027 A1 | 2/1991 |
| DE | 4301113 A1 | 7/1994 |
| DE | 102004052000 A1 | 5/2006 |
| DE | 102005062003 A1 | 6/2007 |
| DE | 102005062388 A1 | 6/2007 |
| DE | 102009029305 A1 | 3/2011 |
| DE | 102010030488 A1 | 12/2011 |
| DE | 102011005957 A1 | 12/2011 |
| DE | 102011075762 A1 | 11/2012 |
| DE | 102014102600 A1 | 9/2014 |
| EP | 0764236 B1 | 8/2001 |

OTHER PUBLICATIONS

Search Report for German Patent Application No. 10 2016 117 733.4, German Patent Office, dated Apr. 19, 2017, 7 pp.

\* cited by examiner

MEASURING DEVICE

CROSS-REFERENCE TO RELATED APPLICATIONS

The present application is related to and claims the priority benefit of German Patent Application No. 10 2015 117 242.9, filed on Oct. 9, 2015, German Patent Application No. 10 2015 121 460.1, filed on Dec. 9, 2015, and German Patent Application No. 10 2016 117 733.4, filed on Sep. 20, 2016, the entire contents of which are incorporated herein by reference.

TECHNICAL FIELD

The present disclosure relates to a measuring device for determining and/or monitoring at least one measurand of a measuring medium.

BACKGROUND

In order to determine the composition of measuring media, in particular liquids, such as pure liquids, liquid mixtures, emulsions or suspensions, various analytical measuring devices are used in process measuring procedures. An analytical measuring device generally comprises a sensing element which is designed to generate a measuring signal dependent upon at least one analytical measurand, as well as a measurement electronic device, which from the measuring signal, determines a measured value representing the current value of the at least one analytical measurand in the measuring medium. The analytical measurand can, for example, be a concentration or activity of an analyte or a parameter dependent upon a concentration or activity of at least one analyte in the measuring medium. An analyte here means one or more substances contained in and, in particular, dissolved in the measuring medium whose concentration in the measuring medium is to be determined or monitored by the analytical sensor. The analyte can even be present in the measuring medium in an undissolved state, and this frequently requires dissolution to be carried out before measurement of the analytical measurand with the sensing element. The measurement electronic device can at least partially be integrated in a measuring transducer, which has a housing with display and input elements, located immediately at the measurement point.

Analytical measuring devices are used in a variety of areas, for example, for monitoring and controlling processes in pharmaceutical, chemical, biotechnical or biochemical production, and even in processes for water conditioning or sewage purification and also in environmental analysis. When an analytical measuring device is used in a process, the measuring medium will usually be contained in a process vessel. In the field of environmental analysis, the measuring medium can also be an open body of water.

A selection of several analytical measuring devices based on different measuring principles is often available for measuring a specific analytical measurand. Each measuring principle has its own specific advantages and disadvantages.

To measure the concentration of a water ingredient, e.g. of a special ion concentration, automatic analyzers are known, for example, which pretreat a sample of the liquid to be analyzed taken from the process for analysis, e.g. by the addition of reagents, and record a measurand dependent upon the concentration of the water ingredient by means of a sensing element in the pretreated sample. The sample to be analyzed is often pretreated inside the analyzers by adding one or a plurality of reagents, thus provoking a chemical reaction in the sample with the participation of the analyte. The reagents are preferably selected such that the chemical reaction can be demonstrated by means of an optical or electrochemical measuring principle, e.g. by means of a photometric sensing element, a potentiometric or an amperometric sensor, or a conductivity sensor. For example, the chemical reaction can cause a coloration of the sample or an emission of luminescent radiation. The color intensity, which can be determined by means of absorption or extinction measurement or the intensity of the luminescent radiation, is in this case a measure of the analytical measurand to be determined. The absorption or extinction for a wavelength correlating to the coloration of the sample may, for example, be determined by photometric means by feeding electromagnetic radiation, such as visible light, from a radiation source into the liquid sample, and receiving it with a suitable detector after transmission through the liquid sample. The detector generates an electrical measurement signal which depends on the intensity of the radiation received and from which a measured value of the analytical measurand can be derived.

Such analyzers are known, for example, from DE 10 22 822 A1, DE 10 2009 029 305 A1 or DE 10 2011 075 762 A1. On the one hand, they deliver very accurate measured values; on the other hand, a relatively long period of time is needed for a measurement cycle which comprises the taking of the sample, the pretreatment of the sample and the determination of a measured value by means of a photometric measurement of the pretreated sample. Said time period can last between 5 and 120 minutes depending on the analytical measurand to be determined. This type of analytical measuring device may therefore only be used with restrictions for monitoring and/or controlling or regulating very dynamic processes.

On the other hand, so-called in-line measuring devices, in particular electrochemical sensors, such as potentiometric ion-selective electrodes (ISEs) or amperometric sensors, are also known for determining the concentration of water ingredients, such devices reacting in close to real time to fluctuations in the value of the measurand. An in-line measuring device is integrated directly into a process vessel in which the process to be monitored is carried out or which contains a process medium being used in the process, and records the measurand directly in the process medium to be monitored. The taking and pretreatment of a sample from a process can therefore be dispensed with for in-line measuring devices. However, in-line measuring devices often comprise an amperometric, potentiometric, photometric or spectrometric sensing element which has a not insignificant cross-sensitivity to other parameters or measurands, in particular to changes in the water matrix. Measured values that are determined using such measuring devices are, therefore, generally subject to a higher degree of measuring error than the measured values determined by an analyzer. In addition, with several ion-selective electrodes an age-related drift occurs which can be compensated for to a certain extent by regular calibration or adjustment of the ion-selective electrodes.

A very similar problem also exists in the field of biological or biotechnological production processes in which microorganisms or their components are used. In such processes it is important for the measurands related to process control, so-called process control parameters and/or product-quality-related parameters or measurands, to be determined near-contemporaneously with the process by means of an appropriate process measuring technology so as to enable a high level of productivity to be achieved by increasing the yield with minimized production runtimes.

A known system concept of this type of process measuring technology for biotechnological applications is based on the use of spectroscopic in-line measuring devices. In this case, a sensing element designed as an in-line sensor is introduced into the process via a suitable port arranged in the wall of a process vessel, for example, via a standard Ingold port. The in-line sensor is therefore in direct contact with the process. The system components of the sensor located in the process must therefore be sterilizable, that is they should advantageously be stable with respect to CIP or SIP processes (the abbreviation CIP stands for "cleaning in process", SIP stands for "sterilization in process") and autoclaving. A spectroscopic sensing element comprises a radiation source that emits electromagnetic measuring radiation which interacts with the process medium and is then measured again by means of a radiation detector of the sensing element. The radiation source and the radiation detector can be located inside the housing of the in-line sensor or inside a unit at a distance from the process or the housing of the sensor, referred to as a spectrometer. In the latter case, the measuring radiation coming from the radiation source is guided along optical fibers from the spectrometer to the sensor housing and the radiation to be measured by the detector is also guided along optical fibers from the sensor housing back to the spectrometer. A distinction can be drawn between UV/Vis, MIR, NIR, and Raman spectroscopy depending on the wavelength range or wave number of the measuring radiation and the type of detection or reception (transmission, reflection, scattering).

The measuring of measured values by means of a spectroscopic in-line measuring device can take place with a rapid rate of measurement and with a short delay between measurement and result which is negligible with respect to process changes. This means that the process can be monitored in close to real time so that the measured values made available by the in-line measuring device can also be used to control or regulate the process.

However, the measurement results obtained using such spectrometric in-line measuring devices only constitute a prediction which can be calculated from the spectroscopic data on the basis of a chemometric model. As a rule, the chemometric model is developed from data determined in the development of the process or from data determined in the past during the implementation of the process. To that end, it is necessary to correlate the spectroscopic data with analytical values of a reference analysis which in most cases does not take place automatically or as part of the process. Quantitative determinations by means of in-line spectroscopy and subsequent chemometric evaluation are known for the measurands glucose content, glutamine content, glutamate content, lactate content, ammonium content, osmolality, viable and total cell density. These types of commercially available systems are offered, for example, by Kaiser Optical Systems Inc. under the product name RAMAN-RXN2 1000 or by Bayer Technology Services GmbH under the product name SpectroBAY.

Alongside the described disadvantage of a complex data generation or evaluation process and protracted correlation analyses, the adaptability of this system concept to process-specific, process-critical or quality-related measurands is severely restricted. Detection limits and accuracies of the measurands which can be determined from spectrometric data are also inadequate in part. They often go hand in hand with a low measuring accuracy particularly with a low concentration and/or high concentrations of interferents, i.e. a not insignificant cross-sensitivity of the in-line sensing element. This is, for example, of great importance for avoiding stress conditions for accurate nutrient determination (e.g. glucose) with a sufficiently low detection level. Stress conditions can lead to reduced microorganism growth, reduced product expression, undesirable by-product expression and/or to a reduction in product quality. It is, therefore, important for the control of bioprocesses to identify such stress conditions early on and to effect controlled intervention in the process in order to prevent or eliminate them.

As an alternative to in-line measuring devices, automated analyzers which determine one or a plurality of this type of measurands by applying analytical methods are also suitable for determining the above-mentioned process control parameters and/or the specified product-quality-related measurands. Just like the aforementioned analyzers which are suitable for determining water ingredients, the automated analyzers suitable for monitoring bioprocesses comprise means for taking samples from the process, means for pretreating the sample to be analyzed, for example by the addition of reagents, which leads to a change in the sample which can be measured by optical or electrochemical sensors. This change can, for example, as already mentioned, be a coloration or the emission of luminescent radiation. These types of analyzers are known, for example, from DE 10 2011 005957 A1 and DE 10 2014 102600 A1. With these devices a fully automated determination of the measured values of relevant measurands is possible. The analysis of the measurement data and the calculation of the current measured values are thereby much less complex than the preparation and application of chemometric models as used in spectrometric in-line measuring devices. Furthermore, in comparison with the aforementioned in-line measurement methods, significantly lower detection/determination limits with a higher degree of accuracy can be selectively achieved, that is, even in the presence of interferents.

However, a disadvantage of these types of analyzer is the long measurement duration or low measuring frequency required due to taking and pretreating samples.

SUMMARY

The object of the present disclosure is to specify a device and a method for determining and/or monitoring at least one measurand of a measuring medium, in particular of a measuring liquid which, on the one hand, is suitable for process control, particularly for control tasks, and which, on the other hand, provides improved measuring accuracy and sufficiently low detection limits.

This object is achieved according to the present disclosure by the device according to claim 1 and the method according to claim 19. Further embodiments are listed in the dependent claims.

The measuring device according to the present disclosure for determining at least one measurand of a measuring medium, in particular of a measuring liquid, includes a first measuring device having a first sensing element in contact with the measuring medium for recording measured values of the at least one measurand, and which is designed to determine, by means of the first sensing element, a first measured value which depends on the at least one measurand of the measuring medium contained in the process vessel, a sampling device which is designed to take a sample from the measuring medium, a second measuring device which comprises at least one second sensing element and which is designed to determine, by means of the second sensing element, a second measured value which depends on the at least one measurand of the sample taken from the measuring medium, and an electronic control device which is designed to receive and to process the first and the second measured values and to carry out a verification, calibration and/or adjustment of the first measuring device with the aid of the second measured value. The measuring medium can, for example, be a measuring liquid. The measuring liquid can, for example, be a pure liquid or a solution, a liquid mixture, an emulsion or a suspension.

In one embodiment, the measuring medium can be contained in a process vessel, wherein the sampling device is designed to take the sample taken from the measuring medium out of the process vessel, and wherein the second measuring device is arranged outside the process vessel and is designed to determine the second measured value of the at least one measurand of the sample taken from the process vessel.

Alternatively, the measuring medium can be present as a measuring liquid in a body of open water. In this case, the sampling device is designed to take a sample from the body of water, and the second measuring device is arranged outside the body of water and is designed to determine the second measured value of the at least one measurand of the sample taken from the body of water. The at least one measurand is preferably an analytical measurand, for example a concentration or activity of an analyte in the measuring medium or a measurand which depends on the concentration or activity of one or a plurality of analytes in the measuring medium.

The sensing element of the first measuring device which is in contact with the measuring medium contained in the process vessel can be integrated in the process vessel, for example, in a wall of the process vessel, as an in-line sensing element. The first sensing element can, for example, be an optical, in particular a photometric or spectrometric, or an electrochemical in-line sensing element, for example, an ion-sensitive electrode, a potentiometric pH sensor, or a conductivity sensor. The sensing element can be in contact with the measuring medium by the fact that the sensing element, in particular a sensor element, such as an analyte-sensitive membrane, or a window or optical element through which measuring radiation is coupled into or decoupled out of the measuring medium, directly touches the measuring medium, for example, being immersed therein. If the first sensing element is a sensing element working on the basis of an optical principle, said element can also be in contact with the measuring medium by the fact that radiation emitted by the measuring medium, transmitted through the measuring medium, or scattered in the measuring medium, is guided to a detector of the sensing element, for example, by activating a radiation source of the sensing element to send out radiation to a radiation path running through the measuring medium between the radiation source and a radiation detector of the sensing element.

The first sensing element has the advantages of an in-line measuring device described herein. It can, for example, with a rapid measuring rate therefore provide current measured values of the measurand to be monitored which can be used to control and/or regulate the process carried out in the process vessel or a process in a process plant encompassing the process vessel.

The second measuring device can be an analyzer arranged outside the process vessel, said analyzer being connected to the sampling device for feeding a sample of the measuring medium taken by the sampling device from the process vessel to the second measuring device. The second measuring device, as a so-called nearline measuring device, is preferably arranged in the proximity of the measuring point where the first measuring device is installed, wherein the sampling device is designed to take a sample of the measuring medium from the sample vessel in the area of the place of installation of the first measuring device and to feed the sample to the analyzer via a liquid line which connects the sampling device to the analyzer. The sample taken from the process vessel by means of the sampling device can then also be filled firstly into a sample vessel by means of the sampling device. This can be designed to be transportable so that the sample can also be transported over a longer distance from the process vessel to the second measuring device. The second measuring device can be designed to take at least a part of the sample, in particular automatically, from the sample vessel. To this end it can comprise a liquid line detachably attachable to the sample vessel and a pump interacting with the liquid line to transport the sample from the sample vessel through the liquid line.

As the second measuring device is not designed as an in-line measuring device, it is possible to subject the sample outside the process vessel to an analytical process which is selective with respect to the measurand to be measured, that is not, or only to a limited extent, impaired by cross-sensitivities, said process providing more accurate measuring results and/or a lower detection limit of the measurand than the first measuring device.

An analytical process is, for example, a process in which the measurand is an analytical measurand, that is, for example, a concentration of an analyte in the measuring medium or a value correlating to the concentration of one or a plurality of analytes in the measuring medium, and in which the sample is then pretreated, for example, by the addition of one or a plurality of reagents and/or by an oxidative decomposition and/or by thermal decomposition in a gas stream so that a chemical reaction product is formed the concentration of which or a value dependent thereupon is quantitatively determined by means of an optical or chemical, for example, electrochemical measuring principle. The analytical measurand to be monitored can be calculated from the determined concentration of the reaction product or the value dependent thereupon. The reaction product formed by the pretreatment can, for example, have a characteristic absorption or fluorescence spectrum, for example, a coloration, or emit luminescent radiation or characteristically reflect or scatter radiation. In this case, the concentration of the reaction product can be determined photometrically or spectrometrically by an absorption measurement or by measuring the intensity of the luminescent radiation, of the reflected or scattered radiation. The concentration of the reaction product can also be determined by a titration or by means of an electrochemical sensing element.

By means of the regular verification, calibration and/or adjustment of the first measuring device using the measured values of high selectivity or measuring accuracy supplied by the second measuring device, a significant improvement in the measured value quality, in particular a reduction in the measurement uncertainty of the measured values supplied by the first measuring device with a rapid measuring rate and available to a control and/or regulation of the process in real time or almost in real time, can be achieved.

In an alternative embodiment, the second sensing element can be designed identically to the first sensing element. Since it is arranged outside the process vessel, it can be regularly calibrated, verified or adjusted without significant effort. In this way it is possible to ensure that the second measured values provided by the second sensing element have a higher measurement quality than the measured values supplied by the first sensing element. Correspondingly, the second measured value can be used to calibrate, verify or adjust the first measuring device.

The first and/or the second measuring device can be designed to record values of a plurality of measurands. In this way, for example, values of a plurality of different analytical measurands can be derived or predicted using a spectrum recorded by one of the sensing elements or spectrometric raw values. The first measuring device, designed as an in-line measuring device, can also be formed by a plurality of in-line sensing elements which are each sensitive to different measurands. Accordingly, a plurality of sensing elements sensitive to the same measurand may also be present. They can, for example, be arranged at different locations in the process vessel and/or be different in kind, that is, based on different measuring principles. The measurands can be analytical measurands and/or additional measurands. Example of additional measurands are temperature of the measuring medium, as well as pressure, fill level and flow rate of the measuring medium in the process vessel.

The second measuring device can be designed to determine and output measured values with a slower measuring rate than the first measuring device. The process vessel may, for example, be a basin, a fermenter or a pipeline and/or a pipe system in a process plant.

The second measuring device can be an automated analyzer which is designed to determine a measured value of the measurand in a sample taken from the process vessel after an analytical process. In particular, it can be designed to pretreat the sample taken from the process vessel, wherein the second sensing element is designed to record a measured value of an additional measurand of the pretreated sample which depends on the measurand to be determined or monitored. As described, a chemical reaction product can be formed by the pretreatment of the sample in an analytical process. In this case, the additional measurand, whose measured values are recorded by means of the second sensing element, is the concentration of the chemical reaction product or a value dependent thereupon. In this embodiment, the second measuring device is configured to deduce from the measured values of the additional measurand the measurand of the measuring medium to be monitored.

The second sensing element can be an optical, in particular spectrometric or photometric, or an electrochemical sensing element. To determine the second measured value of the measurand, the second measuring device can be designed to bring the second sensing element into contact with the potentially pretreated sample taken from the process vessel. This can occur by the sensing element touching the measuring medium, for example, by being immersed therein.

If the second sensing element is designed as an optical sensing element, it can, for example, include a radiation detector which is designed to record a luminescent radiation emitted as a result of the pretreatment of the sample of the analyte or a reaction product of a chemical reaction of the analyte with one or a plurality of reagents. In addition to the radiation detector, the second sensing element may also comprise a radiation source which emits measuring radiation which is recorded after interaction with the pretreated sample by the radiation detector of the second sensing element. The radiation detector is designed to determine one or a plurality of raw values derived from the intensity of a luminescent radiation emitted by the pretreated sample or of a measuring radiation transmitted through the pretreated sample. This embodiment also allows the recording of a spectrum or of absorption values of individual wavelengths depending upon how broadband the radiation emitted by the radiation source is.

If the second sensing element is an optical sensing element of the type described above, the second measuring device may comprise a measuring cell to bring the second sensing element into contact with the pretreated sample, said cell having a transparent wall at least partially for luminescent radiation emitted by the sample, measuring radiation scattered or reflected in the sample, or measuring radiation fed into the pretreated sample by the radiation source. The radiation source and the radiation detector can be arranged in such a way that radiation emitted by the radiation source passes through the pretreated sample contained in the measuring cell and encounters the radiation detector after passing through and interacting with the sample. Alternatively, the second sensing element may also have a sensor housing integrated in the measuring cell which has a transparent wall for the measuring radiation or an opening, possibly tightly sealed by a transparent window or an optical element, through which radiation can be coupled into the measuring cell or decoupled from the measuring cell.

The second measuring device can be designed to capture additional measurands. The second sensing element and/or additional sensing elements of the second measuring device can be used to capture the additional measurand. The second measuring device can, therefore, also provide measured values of additional measurands in addition to the measured values of the measurand monitored by the first measuring device, the in-line measuring device. This enables improved monitoring of the process.

The second measuring device can comprise one or a plurality of liquid containers which contain a reagent or a plurality of reagents which are used to pretreat the sample. Additionally or alternatively, the second measuring device may comprise a breakdown reactor in which the sample can undergo a chemical or thermal decomposition under the addition of one or a plurality of reagents and/or a gas stream. Furthermore, the second measuring device may comprise liquid lines and pumps which are used to take reagents out of the liquid vessels, to mix them with the sample, and to bring the sample thus pretreated into contact with the second sensing element. The second measuring device may comprise an electronic control system for the automatic implementation of the analytical process and for determining the second measured value.

In certain embodiments, the sampling device can be designed in a manner known in prior art, for example as described in DE 202012104908 U1 or DE 1020141026009 A1.

The control system may be an electronic data processing facility with one or a plurality of processors and one or a plurality of memories. It may have a plurality of interfaces via which it can be connected to the first and the second measuring device, as well as to any further measuring devices present and/or any actuators present (for example, one or a plurality of valves with which the sample taking can be controlled) for, in particular bidirectional, communication. Computer programs, which are used for processing output from the first and second measuring device, and for the automated verification and/or calibration and/or adjustment of the first measuring device using the measured values of the second measuring device, and which can be executed by a processor of the control system, may be stored in one or a plurality of memories in the control system. The control system can, for example, take the form of a conventional computer, a mobile device, such as a laptop, a tablet or a smartphone, a transducer, or a programmable logic controller (PLC).

As described further above, the first sensing element of the first measuring device designed as an in-line measuring device can be designed as an optical sensing element. In an embodiment for application in biological or biochemical processes, a spectrometric sensor can, for example, be used as the first sensing element, said sensor having a sensor housing which is integrated in the process vessel, for example, by means of a fitting or a port in the wall of the process vessel. A radiation source, which emits measuring radiation of a predetermined wavelength or a predetermined wavelength range and which feeds into the measuring medium contained in the process vessel, and a radiation detector which is designed to record the measuring radiation after interaction with the measuring medium contained in the process vessel, and to generate an electric signal which depends on an intensity of the measuring radiation recorded by the radiation detector, can be integrated in the housing. The radiation source and the detector can also be arranged outside the sensor housing, in particular in an additional housing arranged at a distance from the sensor housing. In this case, the radiation source and the detector are connected by means of light conductors, in particular fibers. The sensor housing can have an opening or a transparent window for radiation of the measuring radiation used and/or another optical element for coupling measuring radiation in the measuring medium or a corresponding opening, window or an optical element for decoupling the measuring radiation from the measuring medium.

In a further embodiment in which the first sensing element is an electrochemical sensing element, said element can, for example, be a potentiometric sensor, in particular comprising an ion-selective electrode or a pH glass electrode, an ISFET, a ChemFET, or an amperometric sensor, e.g., an oxygen Clark electrode, or a conductivity sensor.

As well as the first sensing element, the first measuring device can comprise measurement electronics which are designed to record raw values which are provided by the sensing element and which depend on the measurand, and to determine from these the first measured value using a model saved in the first measurement electronics. The saved model can be a calibration function, in particular a calibration line, which in each case assigns a measured value to a raw value as a function value. The saved model can also be an, in particular multivariate, chemometric model which assigns a measured value of the measurand to raw values, for example, to an optical spectrum of the measuring medium recorded by means of the first sensing element or to spectrometric values derived from the spectrum or representing the spectrum. For example, a predictive value of the measurand can be determined as a measured value by means of the chemometric model.

As well as the second sensing element, the second measuring device can include a measurement electronic device which is designed to record raw values which are provided by the second sensing element and which depend on the measurand, and to determine from these the second measured value using a model saved in the second measurement electronic device. The saved model can be a calibration function, in particular a calibration line, which in each case assigns a second measured value to a raw value as a function value.

The control system can include at least parts of the first and/or the second measurement electronic device. For example, in at least one embodiment, the first and the second sensing element can be connected to a multichannel transmitter which receives and processes the raw values recorded by both sensing elements or values derived therefrom, in particular digitized values, and determines the first and the second measured value therefrom. The control system can also be designed to control the first measuring device, the second measuring device and/or the sampling device. In a further embodiment, the control system and the first measurement electronic device can be integrated together in an electronic data processing facility, e.g. a computer, or a multichannel transmitter or in a PLC. The control system, or the electronic data processing facility in which the control system is integrated, can be connected to the second measurement electronic device via an interface.

The control system can be designed to automatically carry out a calibration, verification or adjustment of the first measuring device at regular intervals. For example, the control system can be designed to carry out a verification and/or calibration and/or adjustment when each measured value is captured by the second measuring device. Alternatively, a verification, calibration or adjustment can be carried out at longer intervals, for example every day or every week. Here the calibration usually means the determining of a deviation of the first measured value measured by the first measuring device from the second measured value provided by the second measuring device which was accepted as correct.

The verification also comprises the determining of the deviation and its assessment or evaluation. Adjustment means the adapting of the first measuring device in such a way that a model used by the first measuring device to determine a measured value from a raw value supplied by the first sensing element is adapted such that it corresponds to the second measured value provided by the second measuring device and serving as a reference value.

The control system can, for example, be designed to carry out an adjustment in such a way that a model, saved in the first measuring device and/or in the control system and used to assign a measured value of the measurand serving as first measured value to the raw values supplied by the first sensing element, is adapted in such a way that, using the adapted model a value corresponding to the second measured value of the measurand determined by means of the second measuring device and used for adjustment, in particular approximate thereto, or identical thereto, results from the raw values recorded by means of the first sensing element.

In certain embodiments, the sensing element of the first measuring device can be designed to capture a spectrum, in particular a luminescence or an absorption spectrum, of the measuring medium in a predetermined wavelength range, wherein the first measuring device determines, in particular predicts, the first measured value using the recorded spectrum by means of a chemometric model. In this embodiment the control system can be designed to adapt the chemometric model with the aid of the second measured value serving as reference value for the purpose of adjustment. In such an embodiment, the control system can also be designed to establish a chemometric model for monitoring a special process with the aid of measurement data recorded by means of the first measuring device and measured values determined by the second measuring device of one or a plurality of different measurands. In this way the establishing of the chemometric model mentioned above, which is used for process monitoring and control by means of data recorded by the first measuring device, can be carried out automatically by the control system.

To establish the model, the control system can carry out a correlation analysis based on the measurement data provided by the first and the second measuring device, in particular during the first process runs. By means of this analysis, the control system can determine which measurands play a significant role in the process monitoring and control, in particular it can determine the at least first measurand and any additional measurands which should be monitored by means of the spectral data determined by the first measuring device, as well as establish the chemometric model that is used to predict measured values of this measurand to be monitored from the spectral data of the first measuring device.

In at least one embodiment, the sensing element of the first measuring device can be an in-line sensor for recording an ion concentration or a sum parameter of the measuring medium as measurand, in particular an SAC sensor or an ion-selective electrode. In this embodiment, a calibration function, for example a calibration line, can be saved in the measurement electronic device of the first measuring device, said function serving to assign a measured value of the measurand to the raw value recorded by the first measuring device as function value, that is, in such an embodiment, a measured value of the ion concentration or the sum parameter. In such an embodiment, the control system can be set up to adapt, for the purpose of adjusting the first measuring device, the calibration function, in particular a zero point and/or a gradient of the calibration line, by means of the second measured value serving as reference value.

The present disclosure further includes a method for determining and/or monitoring at least one measurand of a measuring medium, in particular a measuring liquid, including recording a first measured value dependent upon the at least one measurand of the measuring medium by means of a first measuring device having a first sensing element which is in contact with the measuring medium for capturing measured values of the at least one measurand, taking a sample of the measuring medium by means of a sampling device, determining a second measured value dependent upon the at least one measurand of the sample of the measuring medium taken from the process vessel by means of a second measuring device which comprises a second sensing element, and calibrating and/or verifying and/or adjusting the first measuring device based on the second measured value by means of an electronic control system designed to receive and to process the first and second measured value.

In at least one embodiment, the measuring medium, in particular the measuring liquid, can be contained in a process vessel, wherein the sample is taken from the process vessel by means of the sampling device, and wherein the second measuring device is arranged outside the process vessel and determines the second measured value in the sample taken from the process vessel. The measuring medium can also be contained as a measuring liquid in a body of water. In this case the sample is taken out of the body of water.

In an embodiment of the method, the control system adjusts the first measuring device by adapting a model saved in the first measuring device and/or in the control system that serves to assign a measured value of the at least one measurand serving as first measured value to raw values recorded by the first sensing element in such a way that, by using the adapted model, a value as first measured value of the at least one measurand, corresponding to the second measured value of the measurand determined by means of the second measuring device and used for adjustment, in particular approximate thereto, or identical thereto, results from the raw values recorded by means of the first sensing element.

In an embodiment, at least one first measured value detected by the first measuring sensor at the same time as the removal (i.e., taking) of a sample, or within a set time window around the time at which a sample of the measuring medium is removed from the process vessel, is at least temporarily saved, and/or raw values used to determine this first measured value are at least temporarily saved. The measured value and/or the raw values may be saved together with information, such as a time stamp, representing the time at which it was or they were recorded. The length of the set time window (i.e., period) is preferably selected to ensure that the composition of the removed/taken sample substantially corresponds to the composition of the measuring medium at the time of detecting the first measured value or the saved first measured value, or the raw values. The length of the time window accordingly depends on the dynamics of the process. Of course, information representing the time of sampling can also be saved. The time of sampling if applicable can be affixed to the removed sample. If the sample, after being removed from the process vessel, is poured by the sampling device into an especially transportable sample container as described above, the time of sampling can be affixed to the sample container. Possibilities for this are an RFID tag and/or an optical code such as a barcode or QR code affixed to the removed sample. The optical code can be designed as a printed code, or also displayed on a display unit such as a display, for example an LCD display. The least one first measured value and/or the corresponding raw values can be saved in a memory of the first measuring device, and/or in a memory of the control device.

For verification or calibration with the second measured value, the control device may use the least one saved first measured value which was detected at the same time as or within the cited time window around the removal or taking of the sample, by means of which the second measured value was determined. Accordingly, the first measuring device is verified or calibrated with the second measured value taking into consideration the point in time at which the first measured value was captured, as well as the point in time of sampling, for example, by performing a back calculation over time using the two time stamps. This is particularly advantageous if a certain time span passes while determining the second measured value.

For adjusting with the second measured value, the control apparatus may use the raw values which were used to determine at least one first measured value and which were detected at the same time as or within the cited time window around the removal or taking of the sample, by means of which the second measured value was determined. Accordingly, the first measuring device is adjusted using the second measured value taking into account the points in time or a back calculation over time.

As initially described, the measured values determined with the first in-line measuring device have a higher measuring frequency than those which were determined with the first measuring device. In an embodiment, an interpolation is performed by the control apparatus with the measured values determined and output at the lower measuring frequency. The interpolation points of the interpolation are the measured values determined with the second measuring device. The interpolation can be performed using a linear function. The interpolation can also be performed by means of a nonlinear function, wherein the nonlinear function describes the dynamics of the measurand within the respective process. With the aid of the interpolation, interpolated measured values of the second measuring device are available at points in time at which no measured value was determined by the second measuring device. With the aid of the interpolation of the second measured values, the first measuring device can accordingly be calibrated, and/or verified, and/or adjusted using the second measured value at a frequency that is higher than the measuring frequency of the second measuring device.

BRIEF DESCRIPTION OF THE DRAWINGS

In the following, the present disclosure will be described in detail with reference to the exemplary embodiments shown in the figures. In the figures.

DETAILED DESCRIPTION

Figure 1:
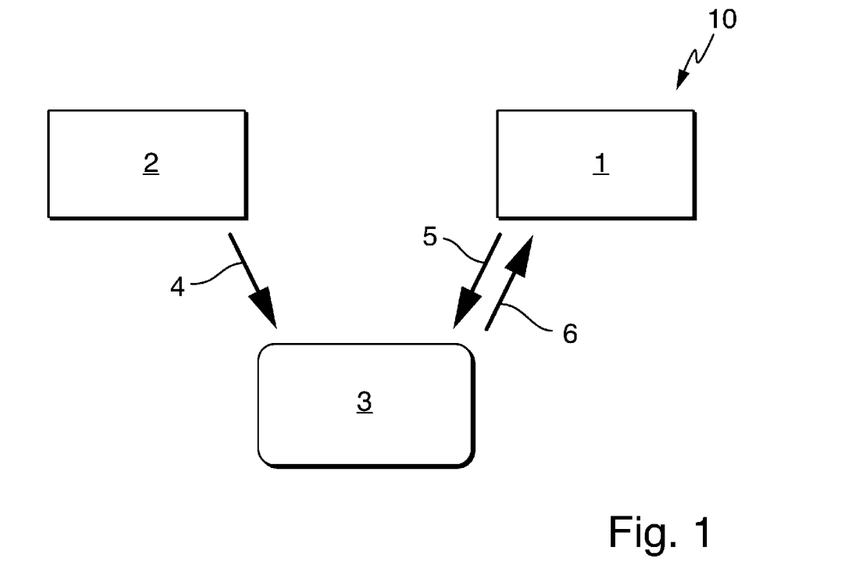
FIG. 1 shows a measuring arrangement with a first and second measuring device and a control apparatus connected thereto.

FIG. 1 schematically portrays a measuring arrangement 10 comprising a first measuring device 1, a second measuring device 2, and a control apparatus 3 that can for example be designed as a multichannel measuring transducer. In the present example, the measuring device 1 is an in-line measuring device that is integrated in a process vessel (not shown) and serves to capture a measurand of a measuring medium contained in the process vessel to perform a process. In the present example, the measuring medium is a measuring liquid. The first measuring device 1 detects measured values of the measurand at a fast measuring cycle such as greater than 60 measured values per minute; however, it exhibits a strong cross-sensitivity to disturbing influences such as changes in the composition of the process medium. The first measuring device 1 can for example comprise an in-line probe as the measuring sensor. In the present example, the measurand to be monitored by the measuring arrangement 10 is an ion concentration in the measuring liquid. A measuring sensor of the first measuring device 1 can have a potentiometric measuring sensor, including an ion-sensitive electrode, and a measuring electronic device that is connected to the measuring sensor and which are designed to capture, digitize and further process raw values generated by the potentiometric measuring sensor, in particular to determine from the raw values a measured value of the ion concentration to be monitored with a calibration function saved in a memory of the measuring electronic device. The raw values of a potentiometric measuring sensor with an ion-selective electrode are for example voltage values which are assigned concentration values by means of the calibration function.

The first measuring device 1 is connected by an interface 5, 6 to the control apparatus 3 which is designed to receive the measured values supplied by the first measuring device 1 and possibly process them further.

The second measuring device 2 has a measuring sensor which is designed to determine the same measurand as the first measuring device 1, or a measurand that can be recalculated into the measurand determined by the first measuring device. In the present example, the second measuring device 2 is designed to detect the ion concentration which can also be determined by means of the first measuring device 1. To this end, the second measuring device 2 is supplied with a sample of the measuring liquid removed from the process. The second measuring device 2 can be designed to determine the measurand by means of an analytical method, such as by automatically pre-treating the sample of the measuring liquid with one or more reagents. In the present example, a chemical reaction is carried out by adding one or more reagents with the participation of the analytes in the measuring liquid, which produces a colored reaction product such that a color emerges in the measuring liquid in the presence of the analytes, i.e., the ions, the concentration of which is to be determined. The second measuring device 2 furthermore includes a photometric measuring sensor that detects the intensity of the color by measuring absorption. The second measuring device 2 furthermore comprises a measuring electronic device connected to the photometric measuring sensor that is designed to further process the raw values representing the absorption of the sample in a given wavelength range that are supplied by the photometric measuring sensor, in particular to digitize the raw values, and to determine from these values measured values of the measurand to be monitored, in this case the ion concentration. For this purpose, a calibration line is saved in the measuring electronic device that plots the raw values against the concentration values. The second measuring device 2 is also connected via an interface 4 to the control apparatus 3. The control apparatus 3 is designed to receive the measured values supplied by the second measuring device 2 and possibly process them further.

A measuring cycle of the second measuring device 2 therefore includes the removal of the sample from the process vessel, the pretreatment of the sample, and the detection of the measured value of the measurand, as well as possibly one or more cleaning or rinsing cycles that serve to clean the parts of the measuring device 2 coming into contact with the liquid in order to thereby prevent cross contaminations. Depending on the measurand to be determined and the analytical method used, the typical duration of such a measuring cycle is about 5 to 60 minutes. The second measuring device 2 therefore detects measured values at a much lower measuring frequency than the first measuring device 1. On the other hand, the measured values of the second measuring device 2 have a significantly lower measuring error than the measured values of the first measuring device 1. In particular, the analytical method of the second measuring device 2 possesses a significantly lower cross-sensitivity to matrix changes than the first measuring device 1 because the chemical processes that cause the coloration of the sample to be detected are generally much more selective than the processes serving to generate the potentiometric measuring signal that occur in a membrane of an ion-selective electrode.

The control apparatus 3 in the present example is designed as a multi-channel measuring transducer or as a PLC. It is designed to receive the measured values captured by the first and second measuring devices 1, 2 via the interfaces 4 and 5, and to perform a calibration, or verification, or adjustment of the first measuring device 1 using a measured value from the second measuring device 2. The control apparatus 3 includes a memory in which a computer program is stored that can be executed by the control apparatus 3 and serves to calibrate, verify and/or adjust the first measuring device 1. The control apparatus 3 can also be partially designed as a multi-channel transmitter and partially as a PLC, wherein the multichannel transmitter is connected to the first and second measuring devices 1, 2 and performs the verification, calibration and/or adjustment, whereas the PLC is used for process control and/or process regulation.

The calibration and/or verification of the first measuring device 1 can include the following: the preparation of an evaluation for the measured values detected with the first measuring device 1; and the preparation of a recommendation for the next time for a verification, calibration and/or adjustment of the first measuring device 1 that is not to be performed in-line. In the verification, calibration and/or adjustment of the first measuring device 1 that is not to be performed in-line, the first measuring device 1 designed as an in-line measuring device is removed from the measuring medium. This is normally done in the context of a servicing task or when the process system is at a standstill.

A calibration or verification is performed by the control apparatus 3 by using a comparison of one or more of measured values of the first measuring device 1 with a current measured value of the second measuring device 2—in particular, to compare a measured value of the second measuring device 2 with one or more measured values of the first measuring device 1 that were detected by the first measuring device 1 at the time of removing the sample used to generate the measured value of the second measuring device 2. For this purpose, the control apparatus 3 saves at least one measured value supplied by the first measuring device 1 at the time of sampling and compares the measured value determined by the second measuring device 2, using the removed sample with the saved measured value of the first measuring device 1. The control apparatus 3 is preferably designed to automatically perform the capture of the measured value and the saving and the comparison of the measured values by using the cited computer program.

To adjust the first measuring device 1, the raw values are saved that were detected at the time of a sampling by the measuring sensor of the first measuring device 1 and serve to determine at least one measured value of the first measuring device 1. The calibration function used by the measuring electronic device of the first measuring device 1 for determining measured values from the raw values is adapted using the measured value of the second measuring device 2 determined using the sample obtained by the same sampling such that the saved raw values are plotted by the adapted calibration function against a measured value that corresponds to the measured value of the second measuring device 2, and is in particular the same. The control apparatus 3 is preferably designed to automatically perform the saving of the raw values and the adjustment by using the cited computer program. The control apparatus 3 can also be designed to simulate the measured values from the first measuring device 1 using the measured values from the second measuring device 2, and/or to simulate the measured values from the second measuring device 2 using the measured values from the first measuring device 1.

The calibration and adjustment can be performed by the control apparatus 3 at regular intervals such as during each measurement by the second measuring device 2.

Figure 2:
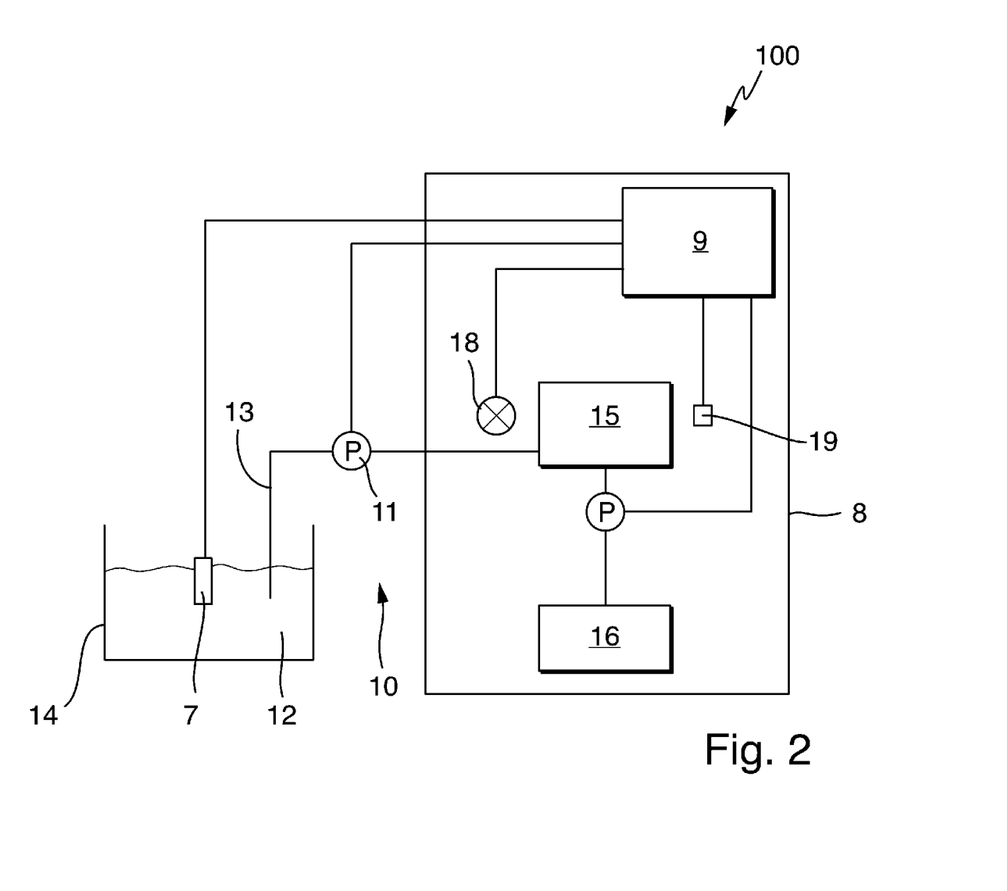
FIG. 2 shows another embodiment of a measuring arrangement with a first measuring device and a second measuring device designed as an analytical measuring device with a control apparatus integrated in the analytical measuring device.

FIG. 2 shows a second example of the present disclosure as a measuring apparatus 100 with a first measuring device and a second measuring device. In the present example, the first measuring device comprises an optical SAC probe 7. The abbreviation SAC stands for the measurand "spectral absorption coefficient" that indicates the absorption or extinction of radiation at one or more wavelengths, in particular the extinction of radiation at the wavelength of 254 nm with reference to 1 meter of irradiated liquid, and that is a measure of the concentration of organic compounds in water as a cumulative parameter. The SAC probe 7 is an optical probe that, to measure extinction, includes one or more radiation sources and one or more radiation detectors that are arranged in a probe housing such that radiation emitted by the radiation source is coupled out of the probe housing into a measuring liquid 12 and, after interacting with the measuring liquid 12, is coupled out of the measuring liquid 12 and conducted to the radiation detector arranged in the probe housing. The SAC probe 7 has a relatively marked cross-sensitivity to changes in the composition of the water matrix. It supplies SAC measured values at a relatively high measuring frequency; in the present example, 2 values per second. The radiation detector of the SAC probe 7 can include one or more photodiodes that emit raw values in the form of a voltage or a current strength. The radiation source of the SAC probe 7 can for example include one or more LEDs (light-emitting diodes). The SAC probe 7 furthermore includes a measuring electronic device that is designed to process, in particular to digitize, the raw values provided by the radiation detector, and to calculate a measured value of the SAC probe 7 using a calibration function saved in a memory of the SAC probe 7. The measured values determined by the SAC probe 7 can be provided in real time to a process controller (not shown in FIG. 2) such as a controller in a sewage treatment plant.

The second measuring device in the present example is an automated COD analytical device 8, which is designed to determine the cumulative parameter COD of a sample of the measuring liquid 12 removed from a process vessel 14. The abbreviation COD stands for the technical expression chemical oxygen demand, and is the amount of a strong oxidant expressed as the oxygen equivalent such as calcium permanganate or calcium dichromate that consumes the oxidizable contents contained in a certain volume of a liquid sample under the reaction conditions of a specified method. Like the SAC value, the COD value is a measure of the concentration of organic contents in water as a cumulative parameter. The COD value and SAC value are mutually convertible.

An analytical device 8 includes a control apparatus 9 which controls the automated sampling from the process vessel 14 and the automated performance of an analytical method for the analytical device 8 to determine the COD, for example. The COD analytical device 8 is connected to a sampling device 10 which includes a pump 11 and a liquid line 13. The pump 11 is designed to remove a sample of the measuring liquid 12 through the liquid line 13 from the process vessel 14, and supply it to a measuring cell 15 of the COD analytical device 8. The analytical device 8 furthermore includes one or more storage containers 16, only schematically indicated in FIG. 2, in which one or more reagents to be supplied to the sample for pretreatment are contained. By means of another pump 17, these reagents can be transported into the measuring cell 15 and there added to the sample. To determine a COD measured value, a strong oxidant such as potassium dichromate is added inter alia to the sample from one of the supply containers 16. The reduced form of the oxidant has a color different from the oxidated form, or an absorption spectrum in the visible spectrum range different from the oxidized form.

To detect the amount of oxidant consumed to oxidize the organic compounds present in the sample, the COD analytical device 8 includes a photometric measuring sensor which has a radiation source 18 and a radiation detector 19. The radiation source 18 and the radiation detector 19 are arranged with reference to the measuring cell 15 such that measuring radiation emitted by the radiation source 18 enters the measuring cell 15 through the transparent wall thereof, passes through the pretreated sample present in the measuring cell 15, exits the measuring cell 15 through the transparent wall thereof, and contacts the radiation detector 19. The radiation source 18 can, for example, include one or more light-emitting diodes. The radiation detector 19 can include one or more photodiodes. The radiation detector 19 is designed to generate an electrical measuring signal that is dependent on the received radiation intensity and, if applicable, output it already in the form of a digital raw measured value to the control apparatus 9.

The control apparatus 9 include means for electronic data processing, in particular a processor and one or more memories in which is stored an operating program serving to control the COD analytical device 8 and the sampling device 10. The control apparatus 9 is connected to the pump 11 of the sampling device 10, a pump 17 serving to convey and meter the reagents from the supply containers 16, and the photometric measuring sensor for in particular bidirectional communication. The control apparatus 9 is designed to control the pump 11 to remove a sample of the measuring liquid 12 and supply it to the analytical device 8 at set time intervals or as needed. Furthermore, the control apparatus 9 is designed to transport a predetermined amount of the reagent(s) required to pretreat the sample into the measuring cell 15 and add it to the sample contained therein. The control apparatus 9 can furthermore be designed to perform cleaning cycles between the measuring cycles in which the parts of the analytical device 8 that come into contact with liquid are rinsed with a rinsing liquid. Furthermore, the control apparatus 9 is designed to control the photometric measuring sensor to capture a measured value and receive the measured value as a raw value from the radiation detector 19 and further process it.

The control apparatus 9 furthermore has an evaluation program which can be run by the control apparatus 9 and is saved in a memory of the control apparatus 9, and which serves to determine a COD measured value from one or more raw values. The control apparatus 9 is in particular designed to determine a COD measured value of the sample using a calibration function present in a memory of the control apparatus 9.

The control apparatus 9 furthermore includes the function of a measuring electronic device of the COD analytical device 8. At the same time, the control apparatus 9 also includes the function of a control apparatus of the measuring apparatus 100. For this purpose, the control apparatus 9 is connected to the SAC probe 7 for bidirectional communication in order to receive the measured values of the SAC probe 7. The control apparatus 9 is designed to perform verification, calibration or adjustment of the SAC probe 7 in a manner highly analogous to that described with reference to FIG. 1. It can furthermore be designed like the control apparatus 3 described with reference to FIG. 1.

Figure 3:
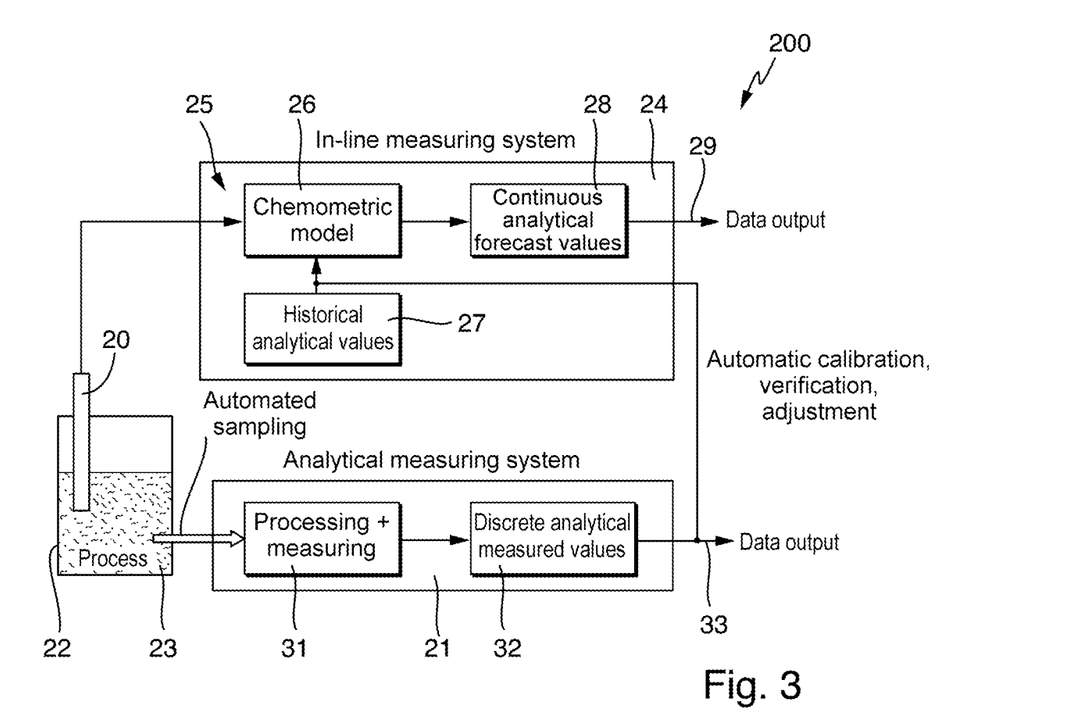
FIG. 3 shows a further embodiment of a measuring arrangement with an in-line measuring device, and an analytical measuring device, and a control apparatus integrated in the in-line measuring device.

FIG. 3 schematically portrays a third example of a measuring apparatus 200 with a first measuring device comprising a spectroscopic probe 20, and an analytical device 21 serving as a second measuring device. The measuring apparatus 200 can be used to monitor a measurand of a biological or biotechnological process that is carried out in a process vessel 22 which is to be kept sterile and is designed for example as a fermenter.

The spectroscopic probe 20 is integrated in the process vessel 22 such that it is in contact with the measuring liquid 23 contained in the process vessel 22. The contact with the measuring liquid 23 can for example be such that the probe 20 comes into contact with the measuring liquid 23, for example, is immersed in it. Alternatively, the contact can also be established in that the probe 20 radiates measuring radiation into the measuring liquid 23 and detects the measuring radiation by means of a radiation detector after interaction with the measuring liquid 23. For example, one or more light-emitting diodes, semiconductor diodes, laser diodes or a laser can serve as the radiation source for the spectroscopic probe 20. The radiation detector can include one or more photodiodes, a photodiode array, or a CCD line or CCD array. The spectroscopic probe 20 can furthermore include a monochromator. The radiation source, radiation detector and monochromator can be arranged in the housing of the spectroscopic probe 20 or in a housing 24 at a distance from the probe 20, wherein in the latter case, the probe 20 is connected by optical fibers to the radiation source and radiation detector.

The radiation detector is designed to convert the radiation intensity that it detects into spectrometric raw values and output them to a measuring electronic device 25 arranged in the present example in the housing 24 at a distance from the probe 20. The measuring electronic device 25 is designed to receive and further process the spectrometric raw values. In particular, the measuring electronic device 25 is designed to evaluate the raw values in order to calculate therefrom a measured value of the measurand to be monitored. The measuring electronic device 25 includes a processor and one or more memories in which an operating program is saved that can be executed by the measuring electronic device 25 and that serves to control the spectroscopic probe 20, as well as one or more evaluation programs serving to evaluate the raw values detected by the spectroscopic probe 20 as spectrometric raw values.

The spectrometric raw values detected by the probe are evaluated by means of a chemometric model 26 stored in the measuring electronic device 25. The chemometric model 26 is based on historical measured data 27 detected over the entire duration of the process in earlier process runs, also termed batches, of the process to be monitored. To create the chemometric model, spectral raw data from a spectrometric probe detected during one or more executed processes, so-called batches, are correlated—frequently as the process develops—with analytical measured values determined with samples that are generally removed manually from the process. The analytical measured values are determined by means of an analytical method such as an immunoassay. The chemometric model 26 thus developed on the basis of earlier batches of the process is stored in the measuring electronic device 25 and is available for evaluating current spectral raw data.

Using the chemometric model 26, a forecast value 28 of the measurand to be monitored is derived by the measuring electronic device 25 from the spectral raw data currently being detected by the probe 20. This value is provided by the data output 29 of the measuring electronic device 25 to a higher-level electronic control apparatus which serves to control the process being carried out in the process vessel 22. The forecast values are available to the control apparatus in real time, or close to real time.

An analytical device 21 serves as a second measuring device for the measuring apparatus 200 and is designed to determine a value of the measurand to be monitored with a sample of the measuring liquid 23 removed from the process vessel 22 by means of an analytical method that for example can include an immunoassay. The analytical device 21 is connected to an automated sampling device 30 which is designed to remove a sample of the measuring liquid 23 from the process vessel 22 under sterile conditions. Such a sampling device is for example described in DE 1020141026009 A1. The analytical device 21 includes a processing and measuring unit 31 that is connected to the sampling device 30 such that the sample removed by the sampling device 30 can be provided to the processing and measuring unit 31.

The processing and measuring unit 31 includes means for pretreating the sample that for example can include the performance of an immunoassay. The pretreatment serves to generate a property, such as a luminescence or a color, of the sample that depends on the measurand to be detected, such as an analyte concentration, and can be detected by physical means. This can be detected by means of a measuring sensor integrated in the processing and measuring unit 31 of the analytical measuring device 21. The analytical device 21 furthermore includes a measuring electronic device 32 that serves to control the processing and measuring and that is designed to determine measured values of the measurand from the raw measured values provided by the measuring sensor, in particular using a calibration function saved in the measuring electronic device 32. The values of the measurand determined in this manner are provided via the data output 33 to the control unit 24 of the in-line measuring device.

The control unit 24 is designed to perform verification, calibration or adjustment of the spectrometric measuring device 20 using the measured values supplied by the analytical device 21. For the adjustment, the chemometric model 26 is adapted based on the measured values provided by the analytical device 21.

The measuring apparatus 200 accordingly makes it possible to monitor biological and biotechnological production processes almost continuously and in real time with regard to compliance with the process specifications. The coupled analytical device 21 enables the automatic calibration, verification and adjustment of the spectroscopy-based in-line measuring system to increase the measuring precision of the continuously-received forecast values based on the spectroscopic measurements. The measurements performed with the analytical device 21 therefore serve to verify the forecast determined by means of the in-line measuring device 20 and adjust the in-line measuring device as needed.

In at least one embodiment, it is possible to perform further analyses with the analytical device 21 in order to determine additional measurands which cannot be determined with the in-line measuring device 20. For this purpose, the analytical device 21 can include additional measuring sensors.

The measuring device 200 can also prepare the chemometric model 26. In this case, the model 26 is prepared during the first process runs, perhaps in a self-learning manner, carried out in the process vessel 22. For this purpose, the measuring electronic device 25 can perform a correlation analysis using the spectral data detected by the probe 20, and analytical measured values of one or more measured variables that are determined by the analytical device 21. With the aid of this analysis, the control unit 24 can determine which measured variables play a major role in monitoring and regulating the process. In particular, they can determine the measured variables that are to be monitored using the spectral data determined by the probe 20, as well as prepare the chemometric model 26 that serves to predict from the spectral data the measured values of these measured variables to be monitored.

The correlation analysis can be carried out in the form of a principal component analysis (PCA). By using the PCA, the influence of the measured variables (i.e., the analytical measured variables and/or other measured variables) on one or more parameters is determined that is/are relevant to the quality of the lots or batches. Typically, such quality-relevant parameters are for example the glucose content and/or the yield in the production of a material. It is also possible to repeatedly perform the correlation analysis and save and evaluate the time characteristic of the correlation analysis. The result of this evaluation can be used in the verification, calibration and/or adjustment of the first measuring device 1 and possibly also employed for process monitoring.

Claimed is:

1. A measuring apparatus for determining at least one measurand of a measuring medium contained in a process vessel comprising:
    a first measuring device including an in-line first measuring sensor integrated into the process vessel as to contact the measuring medium within the process vessel and configured to detect measured values of at least one measurand of the measuring medium, the first measuring device embodied to use the first measuring sensor to determine a first measured value that is dependent on the at least one measurand of the measuring medium;
    a sampling device structured to take a sample of the measuring medium from the process vessel;
    a second measuring device including a second measuring sensor and embodied to use the second measuring sensor to determine a second measured value that is dependent on the least one measurand of the sample taken from the measuring media, wherein the second measuring device is an analyzer disposed outside the process vessel and connected with the sampling device as to enable supplying the sample of the measuring medium taken by the sampling device from the process vessel to the second measuring device, wherein the sampling device is further structured to supply the sample to the second measuring device; and
    an electronic control apparatus in communication with the first measuring device and the second measuring device and programmed to receive and process the first and second measured values and to perform a verification, calibration and/or adjustment of the first measuring device using the second measured value.

2. The measuring apparatus according to claim 1, wherein the at least one measurand is a concentration or activity of an analyte in the measuring medium, or a measurand dependent on the concentration or activity of one or more analytes in the measuring medium.

3. The measuring apparatus according to claim 1, wherein the first measuring sensor is an optical, photometric, spectrometric, or electrochemical in-line measuring sensor.

4. The measuring apparatus according to claim 1, wherein the first measuring device is connected to an electronic process controller via an interface, the electronic process controller programmed to control a process being carried out in the process vessel using the first measured value of the at least one measurand, or in a process being carried out in a processing system comprising the process vessel.

5. The measuring apparatus according to claim 4, wherein the second measuring device is an automated analytical device including:

a measuring cell to which the sample supplied; and at least one reagent with which the sample taken from the process vessel is pretreated, wherein the second measuring sensor is in communication with the measuring cell and is embodied to detect a measured value of a second measurand of the pretreated sample within the measuring cell, which depends on the least one measurand determined by the first measuring device.

6. The measuring apparatus according to claim 5, wherein a chemical reaction product is formed within the pretreated sample, and wherein the second measurand is the concentration of the chemical reaction product, or a variable dependent thereon.

7. The measuring apparatus according to claim 6, wherein the second measuring sensor includes a radiation detector structured to determine an intensity of at least one luminescence radiation emitted by the pretreated sample within the measuring cell or to determine a raw value derived from a measuring radiation transmitted through the pretreated sample within the measuring cell.

8. The measuring apparatus according to claim 6, wherein the second measuring sensor includes a radiation detector structured to determine at least one raw value derived from an intensity of at least one luminescence radiation emitted by the pretreated sample within the measuring cell, or from an intensity of a measuring radiation transmitted through the pretreated sample within the measuring cell.

9. The measuring apparatus according to claim 5, wherein the second measuring device is configured to determine and output measured values at a lower measuring frequency than a first measuring frequency of the first measuring device.

10. The measuring apparatus according to claim 1, wherein the control apparatus is configured to control the first measuring device, the second measuring device, and the sampling device.

11. The measuring apparatus according to claim 1, wherein the first measuring device includes a measuring electronic device structured to detect raw values depending on the at least one measurand and provided by the first measuring sensor and to determine the first measured value from the detected raw values using a model stored in the measuring electronic device.

12. The measuring apparatus according to claim 11, wherein the stored model is a calibration function that assigns a measured value to a raw value as a functional value of the calibration function.

13. The measuring apparatus according to claim 12, wherein the first measuring sensor is an in-line sensor for detecting an ion concentration or a cumulative parameter of the measuring medium.

14. The measuring apparatus according to claim 13, wherein the first measuring sensor is a spectral absorption coefficient probe or an ion-selective electrode.

15. The measuring apparatus according to claim 13, wherein the control apparatus is configured to adapt the calibration function using the second measured value.

16. The measuring apparatus according to claim 1, wherein the first measuring sensor is structured to detect spectrometric raw values representing a luminescence or absorption spectrum of the measuring medium within a predetermined wavelength range, and wherein the first measuring device is configured to derive the first measured value using the detected spectrometric raw values using a chemometric model.

17. The measuring apparatus according to claim 16, wherein the control apparatus is configured to adapt the chemometric model using the second measured value.

18. The measuring apparatus according to claim 16, wherein the control device is configured to prepare the chemometric model using spectral measured data detected by the first measuring device and using measured values determined by the second measuring device of one or more different measured variables.

19. The measuring apparatus according to claim 1, wherein the electronic control apparatus is further programmed to perform the verification, calibration and/or adjustment of the first measuring device using the second measured value of the sample, wherein the sample is taken from the measuring media substantially contemporaneously to the determining of the first measured value.

* * * * *